United States Patent
Gimpel et al.

[19]

[11] Patent Number: 5,877,384
[45] Date of Patent: Mar. 2, 1999

[54] APPARATUS AND PROCESS FOR SEPARATING REACTION EFFLUENT IN THE MANUFACTURE OF CUMENE

[75] Inventors: Harold Edward Gimpel, Sugarland; Eric Wing-Tak Wong, Houston; Kourosh Faiz Ghassemi, Galveston, all of Tex.

[73] Assignee: The M. W. Kellogg Company, Houston, Tex.

[21] Appl. No.: 599,902

[22] Filed: Feb. 12, 1996

[51] Int. Cl.[6] .................................................. C07C 7/04
[52] U.S. Cl. ........................ 585/804; 585/449; 585/450; 208/351; 208/357
[58] Field of Search ...................... 585/323, 448, 585/449, 450, 467, 475, 804; 203/73, 74, 77, 80, 81, 91, 93; 208/351, 354, 357

[56] References Cited

U.S. PATENT DOCUMENTS

| | | | |
|---|---|---|---|
| 3,855,077 | 12/1974 | Bleser et al. | 203/14 |
| 4,008,289 | 2/1977 | Ward et al. | 260/671 R |
| 4,051,191 | 9/1977 | Ward | 260/671 R |
| 4,347,393 | 8/1982 | Miki | 585/323 |
| 4,358,362 | 11/1982 | Smith et al. | 208/91 |
| 4,587,370 | 5/1986 | DeGraff | 585/450 |
| 4,870,222 | 9/1989 | Bakas et al. | 585/323 |
| 4,891,448 | 1/1990 | Garces et al. | 568/628 |
| 4,950,834 | 8/1990 | Arganbright et al. | 585/446 |
| 5,004,841 | 4/1991 | Lee et al. | 568/678 |
| 5,030,786 | 7/1991 | Shamshoum et al. | 585/467 |
| 5,043,506 | 8/1991 | Crossland | 585/449 |
| 5,055,627 | 10/1991 | Smith, Jr. et al. | 585/467 |
| 5,080,871 | 1/1992 | Adams et al. | 422/187 |
| 5,081,323 | 1/1992 | Innes et al. | 585/449 |
| 5,149,894 | 9/1992 | Holtermann et al. | 585/467 |
| 5,176,883 | 1/1993 | Smith, Jr. et al. | 422/211 |
| 5,177,283 | 1/1993 | Ward | 585/446 |
| 5,198,595 | 3/1993 | Lee et al. | 585/467 |
| 5,243,115 | 9/1993 | Smith, Jr. et al. | 585/446 |
| 5,262,576 | 11/1993 | Smith, Jr. | 585/447 |

FOREIGN PATENT DOCUMENTS

| | | |
|---|---|---|
| 9118849 | 12/1991 | WIPO . |
| 9302027 | 2/1993 | WIPO . |

*Primary Examiner*—Glenn A. Caldarola
*Assistant Examiner*—Thuan D. Dang
*Attorney, Agent, or Firm*—The M. W. Kellogg Company

[57] ABSTRACT

An apparatus and process for separating propane and benzene from alkylation reaction products in cumene production. An integrated fractionation tower combines the functions of propane separation, recycle benzene recovery as well as system dewatering to eliminate the need for separate depropanizer and dehydration columns and thus save capital and operating expenses.

10 Claims, 2 Drawing Sheets

APPARATUS AND PROCESS FOR SEPARATING REACTION EFFLUENT IN THE MANUFACTURE OF CUMENE

FIELD OF THE INVENTION

The present invention relates to an apparatus and process for making cumene, and more particularly an apparatus and process for separating propane, benzene and water, if present, from an alkylation reaction effluent in an integrated fractionation tower.

BACKGROUND OF THE INVENTION

Isopropylbenzene (cumene) is widely used for making phenol, acetone and a-methylstyrene. Phenol is a feedstock in phenolic polymer manufacture and acetone is a by-product of the phenol production process. α-Methylstyrene is a feedstock for elastomeric polymers. Cumene is made by a direct alkylation reaction of propylene and benzene in the presence of an acidic catalyst. Cumene is then separated from reactants, by-products, contaminants and inert components in the reaction effluent by fractionation.

Heretofore, cumene manufacturing processes have generally employed an acidic catalyst such as solid phosphoric acid (SPA), aluminum chloride, and the like. Catalysts such as SPA can require the presence of water for activation and produce an extremely corrosive sludge by-product. The use of such sludge-forming catalysts involves special design considerations regarding corrosion, safety and disposal which are expensive to accommodate. Similarly, aluminum chloride catalyst requires anhydrous hydrochloric acid for activation. This corrosive catalyst system requires expensive corrosion-resistant materials in the construction of the reactor, and the spent catalyst also presents disposal problems. More recently, the introduction of new non-corrosive catalysts have reduced the need for the corrosion resistant alloys previously required.

U.S. Pat. No. 4,870,222 to Bakas et al. describes a process for the production of a monoalkylated aromatic compound which minimizes the production of undesirable alkylating agent oligomers, and produces monoalkylaromatics in high yields. The process entails the combination of an alkylation reaction zone, a separation zone and a transalkylation reaction zone wherein the alkylation catalyst and transalkylation catalyst are dissimilar and the catalysts comprise a silica-alumina material.

U.S. Pat. No. 5,198,595 to Lee et al. describes an acidic mordenite zeolite catalyst useful for producing a monoalkylated benzene product. The zeolite catalyst has a silica/alumina molar ratio of at least 40:1.

Other references in interest include U.S. Pat. Nos. 5,243,115, 5,055,627 and 5,176,883 to Smith, Jr. et al., 5,262,576 to Smith, Jr., 5,080,871 to Adams et al., 5,149,894 to Holtermann et al., 5,081,323 to Innes et al., 5,043,506 to Crossland, 4,950,834 to Arganbright et al., 4,347,393 to Miki, 3,855,077 to Bleser et al.; WO 91-18849; and WO 93-02027.

SUMMARY OF THE INVENTION

The functions of multiple individual fractionation columns previously used to separate propane and benzene from the combined alkylation/transalkylation reactor effluent are combined into a single fractionation tower in the present invention to accomplish substantial capital and energy savings over the prior art.

As one embodiment of the present invention, a fractionation tower useful for separating propane and benzene from alkylation reactor products is disclosed. In the present fractionation tower, a first feed stage is provided for receiving cumene alkylation products comprising propane, benzene, cumene, diisopropylbenzene and heavier benzene alkylates. A bottom stage is provided in a heated stripping zone below the first feed stage for recovering a cumene stream containing diisopropylbenzene and heavier benzene alkylates essentially free of propane and benzene. An overhead partial condenser is provided for recovering a mixture of benzene condensate from an overhead vapor stream from the tower and forming a propane stream of reduced benzene content. A first line is provided for refluxing the benzene stream from the separator to a reflux stage of the tower. A second line is provided for recovering a benzene side-draw from a benzene recovery stage disposed between the first and second feed stages.

In a preferred embodiment, the tower is operatively associated with an absorber for contacting the propane stream with a diisopropylbenzene stream to form a propane stream essentially free of benzene and a diisopropylbenzene recycle stream containing benzene suitable for recycle to a cumene alkylation reactor. Any water contained in a make-up benzene stream can be condensed and recovered by the overhead partial condenser to form a mixture of hydrocarbons and water condensate, and a separator is preferably provided for separating the hydrocarbon-water mixture to form hydrocarbon and water streams. A second feed stage is preferably provided above the first feed stage and below the reflux stage for receiving the wet make-up benzene. A side-stripper including a heated stripping zone and a vapor return line can be provided for stripping water from the benzene side-draw to form a dehydrated benzene stream suitable for recycle to the cumene alkylation reactor, and returning vapor from the side-stripper to adjacent the benzene side-draw line, respectively.

As another embodiment, an apparatus for separating cumene alkylation reactor products is provided. The apparatus comprises a raw cumene feed stage for receiving a stream of alkylated benzene containing propane and benzene from the cumene alkylation reactor. A heated stripping zone is provided in fluid communication between the raw cumene feed stage and a bottoms stage. A line is provided for recovering a bottoms product stream from the bottoms stage, comprising alkylated benzene essentially free of benzene. A benzene rectification zone is provided in fluid communication between the raw cumene feed stage and a recycle benzene side-draw stage. A partial condenser and reflux accumulator are provided for partially condensing a vapor stream from the overhead stage to form a liquid hydrocarbon phase and a vapor stream comprising propane and a minor amount of benzene. An absorber is provided for contacting the vapor stream from the partial condenser with an alkylated benzene stream to form a propane stream essentially free of benzene and an alkylated benzene stream containing a minor amount of benzene.

In a preferred embodiment, a water stripping zone is provided in fluid communication between a make-up benzene feed stream, and an overhead product stage is provided to dewater the make-up benzene feed and form an aqueous phase in the reflux accumulator. Lines are provided for decanting the aqueous phase from the accumulator and or refluxing the liquid hydrocarbon phase from the accumulator to the water stripping zone.

As a further embodiment, the present invention comprises a process for separating a reactor effluent comprising propane, benzene, cumene, diisopropylbenzene and heavier benzene alkylate. In step (a), the reactor effluent is fed to a reactor effluent feed stage of a superatmospheric fractionation tower comprising lower, middle, and upper distillation zones, wherein the reactor effluent feed stage is in fluid communication between the lower distillation zone below and the middle distillation zone above. As step (b), the lower distillation zone is heated to strip benzene and form a bottoms product of reduced benzene content comprising cumene, diisopropylbenzene and heavier benzene alkylates. In step (c), a benzene stream is removed as a side draw from the tower at a side-draw stage in fluid communication between the middle distillation zone below and the upper distillation zone above. As tep (d), a vapor stream is removed overhead from the upper distillation zone. In step (e), benzene is condensed from the overhead vapor stream from step (d) to form a benzene-lean propane stream.

In a preferred embodiment, as step (f), a make-up benzene stream is fed to a make-up benzene feed stage of the tower in fluid communication between the upper distillation zone below and a top distillation zone above. In a step (g), water is separated from the benzene condensed in step (e) to form a wet benzene stream. As step (h), the wet benzene stream from step (g) is refluxed to the top distillation zone. In a step (i), the bottom product from step (b) is preferably fed to a cumene column to obtain a cumene product stream essentially free of diisopropylbenzene and heavier benzene alkylates, and a bottoms stream comprising diisopropylbenzene and heavier benzene alkylates. In a step (j), the bottoms stream from step (i) is preferably fed to a diisopropylbenzene column to obtain a diisopropylbenzene stream essentially free of heavier benzene alkylates. As step (k), the propane stream from step (e) is contacted with the diisopropylbenzene stream from step (j) in an absorber to obtain a propane stream essentially free of benzene and a diisopropylbenzene stream containing benzene absorbed from the propane stream. The process can further comprise as step (l), compressing and cooling the propane stream from step (k) to form liquefied petroleum gas. The process can also comprise as step (m) feeding the benzene stream from step (c) to a heated side-stripper to form a dehydrated liquid benzene stream and a benzene vapor stream of enhances water content, and as step (n) returning the benzene vapor stream from step (m) to adjacent the side draw stage of step (c).

In yet another embodiment, the present invention provides an improved method for making cumene. In a method comprising the steps of dehydrating make-up benzene, alkylating benzene and propylene and transalkylating benzene and diisopropyl benzene to form cumene reactor products, distilling the cumene reactor products to form steams of propane, recycle benzene, cumene, recycle diisopropylbenzene and heavier benzene alkylates, and recycling the recycle benzene stream to the alkylating and transalkylation steps and the recycle diisopropylbenzene stream to the transalkylating step, the improvement comprises the steps of: (a) feeding the cumene reactor products and the make-up benzene to separate feed stages of a first superatmospheric fractionation tower; (b) recovering a bottoms product from the first tower comprising cumene, diisopropylbenzene and heavier benzene alkylates essentially free of benzene; (c) recovering the benzene recycle stream as a side-draw from the first tower below the make-up benzene feed stage and above the cumene reactor products feed stage; (d) partially condensing an overhead stream from the first tower to form a propane vapor stream containing a minor amount of benzene and a liquid mixture of benzene and water; (e) separating the liquid mixture into an aqueous stream and a benzene condensate stream; (f) refluxing the benzene condensate stream to the first tower above the make-up benzene feed stage; (g) fractionating the bottoms product from the first tower to form streams of cumene, diisopropylbenzene and heavier benzene alkylates; (h) contacting the propane vapor stream from step (d) with the diisopropylbenzene stream from step (g) to form a propane stream essentially free of benzene and a diisopropylbenzene stream containing a minor amount of benzene; (i) supplying the benzene-containing diisopropylbenzene stream from step (h) as the recycle diisopropylbenzene stream to the transalkylation step.

DETAILED DESCRIPTION OF THE INVENTION

The present invention permits integration of multiple fractionation columns used to recover propane and recycle benzene from alkylation reaction effluent into a single fractionation tower. In addition, the integrated tower can be used to dewater a wet benzene make-up stream and dry the recycle benzene stream. In such a manner, a separate high pressure depropanizer column and associated utility requirements are eliminated, and a separate benzene drying column can be omitted for significant capital and operational savings.

Figure 1:
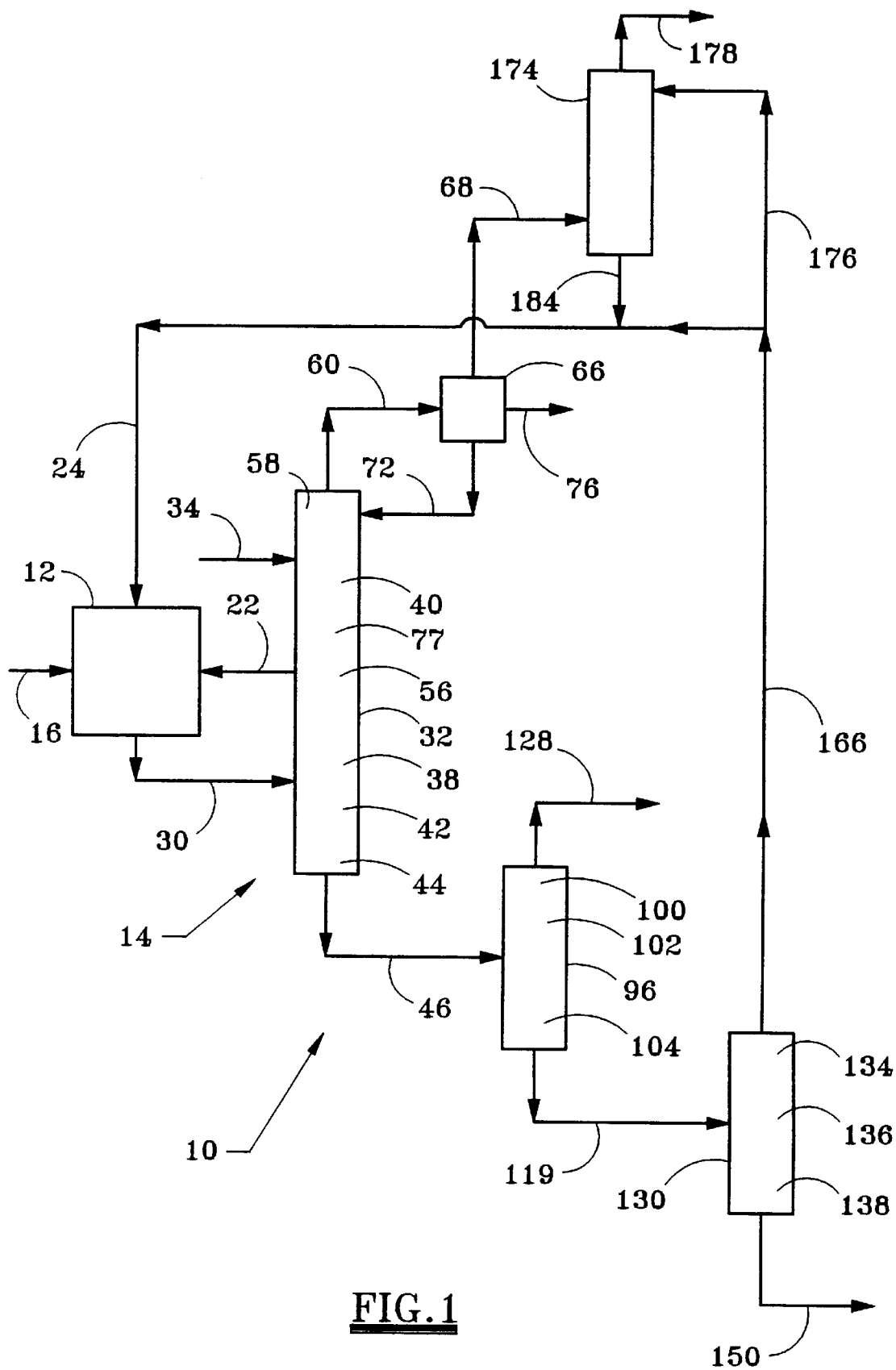
FIG. 1 is a simplified block flow diagram of a cumene process using an integrated tower according to the present invention.

Referring to FIG. 1, a cumene reactor effluent separation process 10 of the present invention comprises an alkylation stage 12 and a cumene recovery stage 14. In the present process, benzene is alkylated by propylene to produce cumene in the presence of a suitable catalyst, preferably a non-corrosive acidic zeolite catalyst. Preferred catalysts are exemplified by a special mordenite zeolite catalyst sold under the trademark 3DDM by the Dow Chemical Co. of Midland, Mich. and described in U.S. Pat. Nos. 5,198,595; 5,004,841; and 4,891,448 which are hereby incorporated herein by reference.

Using the preferred zeolite catalyst, propylene in the feed to the alkylation stage 12 is substantially completely reacted in an excess of benzene to produce monoisopropylbenzene, diisopropylbenzene (DIPB, para and meta isomers) and a very minor amount of triisopropylbenzene (TIPB). The amount of DIPB formed will depend on the quantity of excess benzene over propylene fed to the alkylation stage 12 and alkylation operating conditions. Other alkylbenzenes can be formed from olefinic impurities such as ethylene and butylene in the propylene feed as well as some n-propylbenzene. However, alkylation conditions are preferably chosen to maximize formation of cumene and avoid formation of n-propylbenzene and other impurities.

The preferred zeolite catalyst is also preferably used to transalkylate DIPB to cumene and the transalkylation reaction conditions are chosen to favor cumene formation. Unlike the alkylation reaction which is rapid and exothermic, the transalkylation reaction is slow, equilibrium-limited and thermally neutral. Overall, cumene can be produced at very high purity (99.9 wt %) with a bromine index (for olefinic content) of less than 5.

Propylene is introduced to the alkylation stage 12 via line 16. The propylene stream 16 typically comprises a significant but minor amount of propane which is inert. The amount of propane in the propylene stream 16 can vary from about 1 to about 40 percent by weight depending on the source. Other common impurities include sulfur, propadiene, oxygenates, water, basic nitrogen, and the like. Such impurities are typically removed by pretreatment (not shown) with an adsorbent particulate such as molecular sieve or activated alumina, for example, or in a suitable distillation column.

The propylene stream 16 is combined with a dry benzene reactant stream introduced through line 22 for feed to an alkylation reaction zone (not shown) in the alkylation stage 12. The alkylation reaction zone typically has a fixed catalyst bed wherein the benzene is alkylated to produce cumene, DIPB, and other minor alkylated by-products as mentioned above. A raw cumene reaction effluent primarily comprising cumene, unreacted benzene, and propane but essentially no propylene is typically obtained from the alkylation reaction zone. A DIPB recycle stream 24 is typically fed to a transalkylation reaction zone (not shown) in the alkylation stage 12. The catalyst in the transalkylation zone converts the DIPB and an excess of benzene from line 22 to cumene. The effluents from the alkylation and transalkylation zones are typically combined into a single stream 30 for cumene recovery. Alternatively, the effluent from the alkylation zone can be fed to the transalkylation zone with the recycle DIPB and benzene, in which case the stream 30 is obtained primarily from the transalkylation reaction zone.

In the practice of the present invention, the cumene recovery stage 14 comprises an integrated fractionation tower 32 suitable for separating propane, recovering unreacted benzene and dewatering make-up benzene, if necessary. As is well known, propylene is produced by the catalytic or steam cracking of a hydrocarbon feedstock. Following separation of lighter and heavier components, a raw propylene stream having a significant amount of propane can be obtained. Typically, further distillation in a high pressure depropanizer column is carried out for the cumene process to remove the propane contaminant. However, in the present invention, the propane contaminant is inert and is not beneficially recycled to the alkylation stage 12 in the present process as an aid in heat removal (as in the SPA process). The propylene reactant is essentially completely reacted. Thus, the non-reacting propane can be recovered at a much lower pressure in the tower 32 used to obtain benzene for recycle.

In addition, since water can be present in make-up benzene, such a wet make-up benzene stream is preferably introduced to the tower 32 via line 34 for dewatering to less than 1 ppm (by weight) and thus eliminates the need for separate dehydration pretreatment. Water could otherwise deactivate the reaction catalyst and become a source of corrosion in the system. If water is present in the alkylation effluent stream 30, such as during start-up, or if the stream 30 is water washed as in the aluminum chloride process or is wet for other process reasons, a small, low cost side stripper 36 (see FIG. 2) can also be employed, if desired, to further reduce the water content in benzene recycled to the reaction stage 12. Although more costly, a benzene dehydration pretreatment column (not shown) could alternatively or additionally be used to dry the make-up benzene stream 34, in which case, dewatering in the tower 32 becomes unnecessary.

Figure 2:
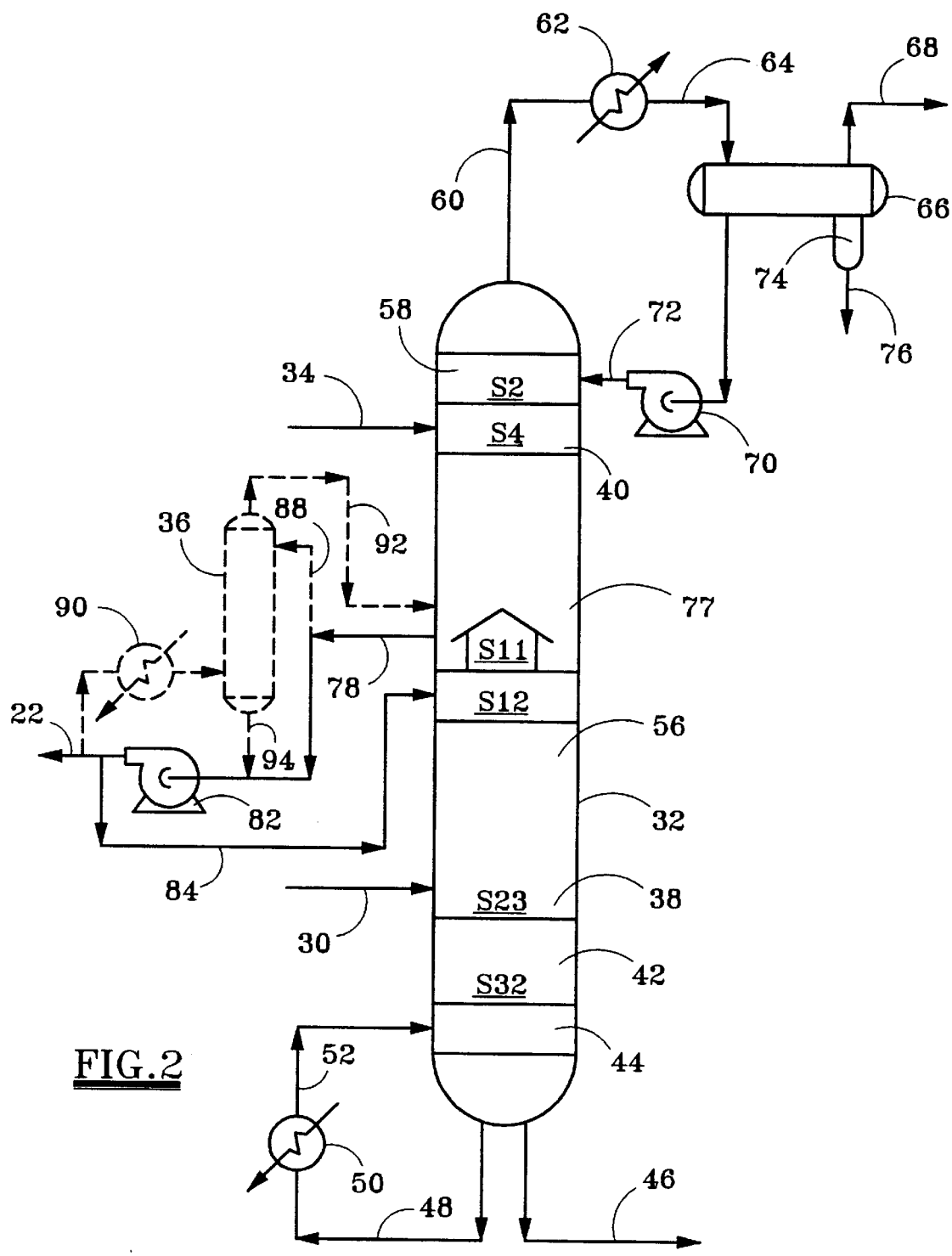
FIG. 2 is a schematic diagram of the integrated tower according to an embodiment of the present invention.

As best seen in FIG. 2, the fractionation tower 32 comprises a first feed stage 38 receiving the raw cumene effluent stream 30 and preferably a second feed stage 40 for receiving a make-up benzene stream 34 which can contain water. (Underlined numerals S2, S4, S11, S12, S23, and S32 shown within the tower 32 in FIG. 2 are used to indicate exemplary tray or theoretical stage locations within the tower 32.) The make-up benzene stream 34, depending on the source, can comprise non-aromatic inerts such as cyclohexane in addition to a varying amount of water.

The tower 32 includes a propane stripping zone 42 having a bottom stage 44 below the first feed stage 38 wherein cumene, DIPB and heavier benzene alkylates are separated and recovered via line 46 as a bottoms stream. Another bottoms stream 48 is supplied to a thermosiphon reboiler 50 to generate a vapor-containing return stream 52. The reboiler 50 is preferably a steam reboiler, but could alternatively use hot oil or be a fired furnace, depending on the tower 32 operation pressure.

The tower 32 also includes a cumene absorption zone 56 having a top stage 58 above the first feed stage 38 wherein propane and water, if present, are concentrated and recovered via overhead line 60. The overhead line 60 is partially condensed by a partial condenser 62 employing a cooling medium such as cooling water or ambient air to condense condensables (benzene and water). A partially condensed tream is introduced via line 64 to an accumulator 66 wherein vapor and liquids are separated. A vapor stream substantially comprising propane s removed via line 68. A benzene-rich liquid stream is pumped by pump 70 as a reflux liquid to the absorption zone 56 via line 72. The accumulator 66 preferably has a leg 74 wherein water which has a higher density than benzene can accumulate. A waste water stream is decanted from the accumulator leg 74 via line 76 for cleanup and disposal.

A side-stream substantially comprising dry benzene is withdrawn from a benzene recovery stage 77 of the tower 32 via line 78 for recycle to the alkylation stage 12. The benzene recycle side-stream 78 can be introduced to a surge drum (not shown) and pumped by a pump 82 to the alkylation stage 12 via line 22 as previously mentioned. To facilitate operation of the tower 32, the liquid in line 78 is preferably drawn off using a chimney tray, and returned below the sidedraw tray by the pump 82 via line 84. A purge stream (not shown) can be withdrawn from the recycle benzene stream 22 to reject any inert alkanes, such as, for example, i-butane, n-pentane, 3-methylpentane, 3-methylhexane, 2,3-dimethylpentane, n-hexane, cyclohexane, n-nonane, and the like.

Prior to circulation to the alkylation stage 12, the benzene side-stream 78 can be dehydrated, as mentioned above, if desired, by the optional side-stripper 36. Thus the benzene side-stream 78 can be introduced via line 88 to the side-stripper 36 wherein additional water is removed by a stripping vapor generated by a reboiler 90. A water-enriched overhead vapor is returned to the benzene recovery zone 77 via line 92. An essentially anhydrous benzene stream, thus formed, is recycled to alkylation stage 12 via line 94. Where the make-up benzene stream is dried in the pretreatment dehydration column (not shown), dry-make-up benzene could be combined directly with the recycle benzene stream 22.

The fractionation tower 32 preferably has an operating pressure between 0.2 and 6.0 MPa(g) and can be made of carbon steel due to a generally non-corrosive environment. A relatively large number of theoretical stages is required and approximately 33 are preferred with the first feed point 38 at about the twenty-third stage S23 (from the top), the second feed point 40 at about the fourth stage S4, and the benzene recovery point 77 at about the eleventh stage S11 (see FIG. 2).

The cumene-rich bottoms steam 46 is fed to a cumene recovery column 96. The cumene column 96 comprises a DIPB absorption zone 100 above a feed stage 102 and a cumene stripping zone 104 below the feed point 102. A benzene-containing stream can be removed overhead and substantially condensed by a condenser (not shown). A liquid benzene-containing stream can be accumulated in a surge drum (not shown) and pumped as a reflux liquid to the absorption zone 100. A portion of the reflux stream can be recycled to the benzene recovery tower 32. Non-condensable components lighter than benzene are removed via a small purge line (not shown) for disposal. The condenser preferably employs low pressure boiler feed water as cooling medium and can generate low pressure steam.

A DIPB-rich bottoms stream is withdrawn from the cumene column 96 via line 119 and pumped through a reboiler (not shown) to generate reboil vapor. The vapor stream is returned to the stripping zone 104. The reboiler is preferably a steam heated reboiler, but could be a fired furnace or heated with hot oil.

A side stream substantially comprising a purified cumene product can be withdrawn from the cumene column 96 via line 128. The cumene product stream 128 is preferably cooled and pumped to a storage facility (not shown).

The DIPB-rich bottoms stream 119 is pumped to a DIPB recovery column 130. The DIPB column 130 comprises a light impurity absorption zone 134 above a feed stage 136 and a DIPB stripping zone 138 below the feed point 136. A stream (not shown) containing components lighter than DIPB can be removed overhead, substantially condensed and accumulated in a surge drum (not shown). A light liquid impurity stream can be used as a reflux liquid to the absorption zone 134. A small purge stream (not shown) of light liquid impurity components can be removed in a continuous fashion from the surge drum to maintain a subatmospheric pressure in the DIPB column 130. The condenser preferably uses ambient air as a cooling medium.

A bottoms stream containing heavy components is removed from the DIPB column 130 via line 150, and a portion thereof can be directed to a reboiler (not shown) to generate reboil vapor. The vapor stream is returned to the stripping zone 138. The reboiler can preferably employ the cumene column reboil vapor or liquid as a heating medium. The rest of the column bottoms in line 150 is removed for disposal as a fuel oil, for example. A portion of the reflux liquid stream (not shown) can also be diverted to fuel oil via the line 150.

A side stream substantially comprising a purified DIPB product is withdrawn from the DIPB column 130 via line 166 and fed to the alkylation stage 12 for transalkylation into cumene. Prior to transalkylation however, all or a portion of the DIPB stream 166 is used as a liquid absorbent for absorbing benzene from the propane-rich stream 68. The DIPB absorbent stream 166 can be cooled by a cooler (not shown) and introduced to an upper end of a benzene absorption column 174 via line 176. The cooler can preferably employ cooling water as a cooling medium. In the absorption column 174, the propane-rich vapor stream 68 is countercurrently contacted with the cooled liquid DIPB stream 176 to absorb residual benzene from the vapor stream 68.

A substantially benzene free propane stream is removed overhead via line 178 for further processing in a gas processing unit (not shown) depending on the initial propane content of the propylene feed 16. If the propane content of the propylene feed 16 is relatively high, the propane stream 178 can be liquefied. In this case, a liquefied propane gas (LPG) product is produced. If the initial propane content in the propylene feed stream 16 is relatively low or if propane fuel gas is preferable to LPG product, the propane stream 178 can be used in a fuel gas system (not shown). A DIPB-rich bottoms stream is removed from the absorber 174 via line 184, combined with that portion of the DIPB stream 166 not used as absorbent, if any, and directed via line 24 to the alkylation stage 12.

EXAMPLE 1

A non-corrosive cumene manufacture process (see FIGS. 1 and 2) based on the preferred zeolite catalyst employing the integrated tower 32 of the present invention to recover benzene and separate propane is simulated by computer algorithm using a 31,750 kg/hr (69,850 lb/hr) cumene production rate as basis for the calculations. The propylene feed contains 5 weight percent propane. The calculated design specifications of the tower 32 are 33 theoretical trays in a tower with a 2.13 m (7 ft) diameter top portion and a 2.59 m (8.5 ft) bottom portion. Purified benzene is optimally recovered at tray 11. Reaction effluent is optimally introduced at tray 23. The calculated design specifications of the absorption column 174 are 10 trays and a 0.457 m (1.5 ft) diameter. Results in terms of feed, product and by-product stream compositions are given in Table 1. Calculated utility requirements are presented in Table 3.

EXAMPLE 2

A similar non-corrosive cumene manufacturing process to the process of Example 1 is simulated by computer algorithm except that the composition of one of the feed streams differs, the propylene contains 30 weight percent propane. The dimensions of the tower 32 are the same as in Example 1, but the diameter of the absorption column 174 increases to 0.762 m (2.5 ft) due to the larger propane flow. Results in terms of feed, product and by-product stream compositions are presented in Table 2. Energy utilization is presented in Table 3 with the data from Example 1.

TABLE 1

| Stream | | Fresh Propylene 16 | Make-up Benzene 34 | Tower Feed 30 | Tower Overhead 68 | Condensed Water 76 | DIPB To Absorber 176 | Absorber Overhead 178 | Absorber Bottoms 184 | Tower Sidedraw 22 | Tower Bottoms 46 |
|---|---|---|---|---|---|---|---|---|---|---|---|
| Temperature (°F.) | | 70 | 70 | 300 | 119 | 119 | 95 | 118 | 140 | 272 | 450 |
| Pressure (psig) | | 200 | 150 | 200 | 38.9 | 38.9 | 50 | 26.3 | 28.3 | 200 | 50.3 |
| Component | MW | | | | FLOW RATE (LB/HOUR) | | | | | | |
| Propane | 44 | 1,298 | | 1,490 | 1,412 | | | 1,298 | 114 | 78 | |
| Propylene | 42 | 24,668 | | | | | | | | | |
| Cyclohexane | 84 | | 35 | 11,743 | 2 | | | | 2 | 11,776 | |
| Benzene | 78 | | 46,026 | 92,069 | 245 | | | 0 | 245 | 137,850 | |
| EB | 106 | | | 3 | | | | | | | 3 |
| Cumene | 120 | | | 69,938 | | | 2 | | 2 | 61 | 69,877 |
| NPB | 120 | | | 9 | | | | | | | 9 |
| BB | 134 | | | 6 | | | | | | | 6 |
| P-Cymene | 134 | | | 36 | | | | | | | 36 |
| M-Cymene | 134 | | | 18 | | | | | | | 18 |
| C11 | 148 | | | 801 | | | 49 | | 49 | | 801 |
| P-DIPB | 162 | | | 20,085 | | | 1,250 | 2 | 1,248 | | 20,085 |
| M-DIPB | 162 | | | 10,042 | | | 625 | 1 | 624 | | 10,042 |
| C6-Benzene | 162 | | | 386 | | | 23 | | 23 | | 386 |
| TIPB | 204 | | | 15 | | | 1 | | 1 | | 15 |
| Toluene | 92 | | 37 | | | | | | | 37 | |
| Heavies | 240 | | | 83 | | | 0 | | 0 | | 83 |
| Water | 18 | | 22 | | 20 | 2 | | 20 | | <1 PPM | |
| TOTAL | | 25,966 | 46,120 | 206,723 | 1,678 | 2 | 1,950 | 1,321 | 2,307 | 149,802 | 101,360 |

TABLE 2

| Stream | | Fresh Propylene 16 | Make-up Benzene 34 | Tower Feed 30 | Tower Overhead 68 | Condensed Water 76 | DIPB To Absorber 176 | Absorber Overhead 178 | Absorber Bottoms 184 | Tower Sidedraw 22 | Tower Bottoms 46 |
|---|---|---|---|---|---|---|---|---|---|---|---|
| Temperature (°F.) | | 70 | 70 | 300 | 121 | 121 | 95 | 118 | 142 | 264 | 450 |
| Pressure (psig) | | 350 | 150 | 350 | 38.9 | 38.9 | 50 | 26.3 | 28.3 | 350 | 50.3 |
| Component | MW | | | | FLOW RATE (LB/HOUR) | | | | | | |
| Propane | 44 | 10,577 | | 12,094 | 11,484 | | | 10,575 | 909 | 610 | |
| Propylene | 42 | 24,680 | | | | | | | | | |
| Cyclohexane | 84 | | 35 | 11,740 | 29 | | | | 29 | 11,746 | |
| Benzene | 78 | | 46,037 | 93,919 | 2,038 | | | 1 | 2,037 | 137,918 | |
| EB | 106 | | | 3 | | | | | | | 3 |
| Cumene | 120 | | | 69,939 | | | 14 | | 14 | 62 | 69,877 |
| NPB | 120 | | | 9 | | | | | | | 9 |
| BB | 134 | | | 6 | | | | | | | 6 |
| P-Cymene | 134 | | | 36 | | | | | | | 36 |
| M-Cymene | 134 | | | 18 | | | | | | | 18 |
| C11 | 148 | | | 800 | | | 385 | | 385 | | 800 |
| P-DIPB | 162 | | | 20,085 | | | 9,939 | 18 | 9,921 | | 20,085 |
| M-DIPB | 162 | | | 10,042 | | | 4,970 | 9 | 4,961 | | 10,042 |
| C6-Benzene | 162 | | | 386 | | | 185 | | 185 | | 386 |
| TIPB | 204 | | | 15 | | | 4 | | 4 | | 15 |
| Toluene | 92 | | 37 | | | | | | | 37 | |
| Heavies | 240 | | | 83 | | | 3 | | 3 | | 83 |
| Water | 18 | | 23 | | 21 | 3 | | 21 | | <1 PPM | |
| TOTAL | | 35,257 | 46,133 | 219,175 | 13,573 | 3 | 15,500 | 10,624 | 18,448 | 150,373 | 101,359 |

As seen in Table 3, the utilities consumptions are nearly identical in Examples 1 and 2; there is only a slight penalty for more propane in the propylene feed as long as the propane is obtained as a vapor from the tower 32. Utilities increase for the Example 2 case if the gas is compressed and condensed to produce LPG. Overall capital costs and utilities remain lower for the integrated tower 32 as compared to the individual columns of the prior art design.

TABLE 3

Utility Summary

Single Column Design

| Description | 5% Propane (Example 1) | | | 30% Propane (Example 2) | | |
|---|---|---|---|---|---|---|
| | HP Steam lb/hr | CW gpm | Electricity kW | HP Steam lb/hr | CW gpm | Electricity kW |
| Tower Condenser 62 | | 2,219 | | | 2,247 | |
| Tower Reboiler 50 | 47,737 | | | 47,599 | | |
| Absorber Feed Cooler (not shown) | | 5 | | | 37 | |
| DIPB Cooler (not shown) | | 23 | | | 182 | |
| Recycle Benzene Pumps 82 | | | 56 | | | 56 |
| Tower Reflux Pumps 48 | | | 22 | | | 22 |
| DIPB Absorber Pumps (not shown) | | | 8 | | | 11 |
| TOTAL | 47,737 | 2,247 | 84 | 47,599 | 2,466 | 90 |

The present cumene manufacturing process and apparatus are illustrated by way of the foregoing description which is intended as a non-limiting illustration, since many variations will become apparent to those skilled in the art in view thereof. It is intended that all such variations within the scope and spirit of the appended claims be embraced thereby.

We claim:

1. A process for separating a reactor effluent comprising propane, benzene, cumene, diisopropylbenzene and heavier benzene alkylate, comprising the steps of:
   (a) feeding the reactor effluent to a reactor effluent feed stage of a superatmospheric fractionation tower comprising lower, middle, and upper distillation zones, wherein the reactor effluent feed stage is in fluid communication between the lower distillation zone below and the middle distillation zone above;
   (b) heating the lower distillation zone to strip benzene and form a bottoms product of reduced benzene content comprising cumene, diisopropylbenzene and heavier benzene alkylates;
   (c) removing a benzene stream as a side draw from the tower at a side-draw stage in fluid communication between the middle distillation zone below and the upper distillation zone above;
   (d) removing a vapor stream overhead from the upper distillation zone;
   (e) condensing benzene from the overhead vapor stream from step (d), to form a benzene-lean propane stream;
   feeding a make-up benzene stream containing water to a make-up benzene feed stage of the tower in fluid communication between the upper distillation zone below and a top distillation zone above;
   (g) separating water from the benzene condensed in step (e) to form a wet benzene stream; and
   (h) refluxing the wet benzene stream from step (g) to the top distillation zone.

2. The process of claim 1, further comprising the steps of:
   (i) feeding the benzene stream from step (c) to a heated side-stripper to form a dehydrated liquid benzene stream and a benzene vapor stream of enhanced water content; and
   (j) returning the benzene vapor stream from step (i) to adjacent the side draw stage of step (c).

3. The process of claim 2, further comprising the steps of:
   (k) feeding the benzene stream from step (c) to a heated side-stripper to form a dehydrated liquid benzene stream and a benzene vapor stream of enhanced water content; and
   (l) returning the benzene vapor stream from step (k) to adjacent the side draw stage of step (c).

4. A Process for separating a reactor effluent comprising propane, benzene cumene, diisopropylbenzene and heavier benzene alkylate, comprising the steps of:
   (a) feeding the reactor effluent to a reactor effluent feed stage of a superatmospheric fractionation tower comprising lower, middle, and upper distillation zones, wherein the reactor effluent feed stage is in fluid communication between the lower distillation zone below and the middle distillation zone above;
   (b) heating the lower distillation zone to strip benzene and form a bottoms product of reduced benzene content comprising cumene, diisopropylbenzene and heavier benzene alkylates;
   (c) removing a benzene stream as a side draw from the tower at a side-draw stage in fluid communication between the middle distillation zone below and the upper distillation zone above;
   (d) removing a vapor stream overhead from the upper distillation zone;
   (e) condensing benzene from the overhead vapor stream from step (d), to form a benzene-lean propane stream;
   (f) feeding the bottoms product from step (b) to a cumene column to obtain a cumene product stream essentially free of diisopropylbenzene and heavier benzene alkylates, and a bottoms stream comprising diisopropylbenzene and heavier benzene alkylates;
   (g) feeding the bottoms stream from step (f) to a diisopropylbenzene column to obtain a diisopropylbenzene stream essentially free of heavier benzene alkylates; and
   (h) contacting the propane stream from step (e) with the diisopropylbenzene stream from step (g) in an absorber to obtain a propane stream essentially free of benzene and a diisopropylbenzene stream containing benzene absorbed from the propane stream.

5. The process of claim 4, further comprising the steps of:
   (i) feeding a make-up benzene stream containing water to a make-up benzene feed stage of the tower in fluid communication between the upper distillation zone below and a top distillation zone above;
   (j) separating water from the benzene condensed in step (e) to form a wet benzene stream;
   (k) refluxing the wet benzene stream from step (i) to the top distillation zone.

6. The process of claim 5, further comprising the steps of:
   (l) feeding the benzene stream from step (c) to a heated side-stripper to form a dehydrated liquid benzene stream and a benzene vapor stream of enhanced water content; and
   (m) returning the benzene vapor stream from step (l) to adjacent the side draw stage of step (c).

7. The process of claim 4, further comprising the step of:
   (i) compressing and cooling the propane stream from step (h) to form liquefied petroleum gas.

8. The process of claim 7, further comprising the steps of:
   (j) feeding the benzene stream from step (c) to a heated side-stripper to form a dehydrated liquid benzene stream and a benzene vapor stream of enhanced water content; and (k) returning the benzene vapor stream from step (j) to adjacent the side draw stage of step (c).

9. The process of claim 4, further comprising the steps of:

(i) feeding the benzene stream from step (c) to a heated side-stripper to form a dehydrated liquid benzene stream and a benzene vapor stream of enhanced water content; and (j) returning the benzene vapor stream from step (i) to adjacent the side draw stage of step (c).

10. In a method comprising the steps of dehydrating make-up benzene, alkylating benzene and propylene and transalkylating benzene and diisopropyl benzene to form cumene reactor products, distilling the cumene reactor products to form streams of propane, recycle benzene, cumene, recycle diisopropylbenzene and heavier benzene alkylates, and recycling the recycle benzene stream to the alkylating and transalkylation steps and the recycle diisopropylbenzene stream to the transalkylating step, the improvement comprising the steps of:

(a) feeding the cumene reactor products and the makeup benzene to separate feed stages of a first superatmospheric fractionation tower;

(b) recovering a bottoms product from the first tower comprising cumene, diisopropylbenzene and heavier benzene alkylates essentially free of benzene;

(c) recovering the benzene recycle stream as a sidedraw from the first tower below the make-up benzene feed stage and above the cumene reactor products feed stage; (d) partially condensing an overhead stream from the first tower to form a propane vapor stream containing a minor amount of benzene and a liquid mixture of benzene and water;

(e) separating the liquid mixture into an aqueous stream and a benzene condensate stream;

(f) refluxing the benzene condensate stream to the first tower above the make-up benzene feed stage;

(g) fractionating the bottoms product from the first tower to form streams of cumene, diisopropylbenzene and heavier benzene alkylates;

(h) contacting the propane vapor stream from step (d) with the diisopropylbenzene stream from step (g) to form a propane stream essentially free of benzene and a diisopropylbenzene stream containing a minor amount of benzene;

(i) supplying the benzene-containing diisopropylbenzene stream from step (h) as the recycle diisopropylbenzene stream to the transalkylation step.

* * * * *